United States Patent [19]

Kanda et al.

[11] Patent Number: 5,728,830
[45] Date of Patent: Mar. 17, 1998

[54] FARNESYLTRANSFERASE INHIBITOR

[75] Inventors: Yutaka Kanda; Yutaka Saitoh, both of Machida; Kazuhito Akasaka, Shizuoka; Tamio Mizukami; Hirofumi Nakano, both of Machida, all of Japan

[73] Assignee: Kyowa Hakko Kogyo Co., Ltd., Tokyo, Japan

[21] Appl. No.: 436,458

[22] PCT Filed: Sep. 20, 1994

[86] PCT No.: PCT/JP94/01543

§ 371 Date: May 22, 1995

§ 102(e) Date: May 22, 1995

[87] PCT Pub. No.: WO95/08542

PCT Pub. Date: Mar. 30, 1995

[30] Foreign Application Priority Data

Sep. 22, 1993 [JP] Japan .................... 5-236179

[51] Int. Cl.$^6$ .................... C07D 241/08; C07D 285/15
[52] U.S. Cl. .................... 544/5; 544/385
[58] Field of Search .................... 544/385, 5; 514/255, 514/222.8

[56] References Cited

U.S. PATENT DOCUMENTS

| | | | |
|---|---|---|---|
| 3,562,253 | 2/1971 | Trown | 260/239.3 |
| 3,883,561 | 5/1975 | Michel et al. | 260/243 |
| 4,007,190 | 2/1977 | Shen et al. | 260/268 DK |

FOREIGN PATENT DOCUMENTS 2029306  12/1970  Germany.

OTHER PUBLICATIONS

Jiang et al, Chemical Abstracts 120:323008 (1994).
Pita Boente et al, Chemical Abstracts, vol. 115:179041 (1991).
Waring et al, Chem. Abstr. 113:127923 (1990).
Shimazaki et al, Chem. Abstr. 111:439386 (1989).
Shimazaki et al, Chem. Abstr. 107:228452 (1987).
Journal of Antibiotics, vol. 45, pp. 1802 to 1805 (1992).
Aust. J. Chem., vol. 46, No. 11, 1993, Australia, pp. 1743-1754, Jiang et al.
Journal of the Chemical Society, Chemical Communications 1983, Letchworth GB pp. 812-813, G.W. Kirby, et al. "Structure and Synthesis of CIS-3, 6-Dibenzyl-3,6-Bis(Methylthio)-Piperazine-2,5-Dione".
Chemical Abstracts, vol. 111, No. 5, 1989, Columbus, Ohio, U.S. Abstract No. 39386r, pp. 604-605 Shimazaki et al.
Chemical Abstracts, vol. 85, No. 3, 1976, Columbus, Ohio, U.S. Abstract No. 21473b, pp. 704-705 Matsunari et al.
Biochem. Biophys. Res. Commun., vol. 33, No. 3, 1968, USA, pp. 402-407 Trown.

*Primary Examiner*—John M. Ford
*Attorney, Agent, or Firm*—Antonelli, Terry, Stout & Kraus, LLP

[57] ABSTRACT

The present invention relates to a farnesyltransferase inhibitor and an antitumor agent comprising, as an active ingredient, a piperazinedione derivative represented by formula (I):

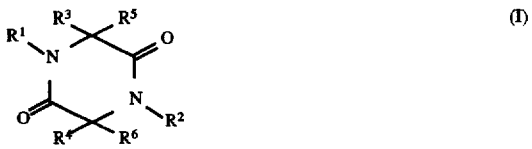

wherein $R^1$ and $R^2$ independently represent lower alkyl, lower alkoxyalkyl, substituted or unsubstituted aryl, or aralkyl; $R^3$ and $R^4$ independently represent mercapto, lower alkanoylthio, aroylthio, lower alkoxycarbonylthio, or aryloxycarbonylthio, or alternatively $R^3$ and $R^4$ are combined together to form disulfide; and $R^5$ and $R^6$ independently represent hydrogen, lower alkyl, lower alkoxyalkyl, hydroxyalkyl, lower alkanoyloxyalkyl, aroyloxyalkyl, aralkyloxyalkyl, or aralkyl.

5 Claims, No Drawings

FARNESYLTRANSFERASE INHIBITOR

This application is a national stage application under 35 U.S.C. §371 of PCT/JP94/01543, filed Sep. 20, 1994, published as WO95/08542 Mar. 30, 1995.

TECHNICAL FIELD

The present invention relates to a farnesyltransferase inhibitor comprising a piperazinedione derivative as an active ingredient, which has antitumor activity and is useful as an antitumor agent.

BACKGROUND ART

The ras oncogene undergoes point mutation in various tumor tissues in humans and is detected as an activated form capable of transforming normal cells. It is essential for the exhibition of transforming activity by the ras oncogene product that the 12th, 13th, or 61st amino acid should undergo mutation and also the cysteine residue at the C terminal region should be farnesylated for the membrane association of the ras oncogene product. This reaction is catalyzed by farnesyltransferase. Accordingly, a farnesyltransferase inhibitor is expected to inhibit the function of the ras oncogene product and thereby to possess antitumor activity.

Known farnesyltransferase inhibitors having a piperazinedione skeleton include gliotoxin and acetylgliotoxin [J. Antibiotics, 45, 1802 (1992)].

Some of the piperazinedione derivatives according to the present invention are known to have activities such as antagonistic activity against platelet activating factors (Japanese Published Unexamined Patent Application No. 233675/86) and antibacterial activity (Get. Offen. 2029306). However, there has been no report on their farnesyltransferase inhibitory activity or antitumor activity.

DISCLOSURE OF THE INVENTION

The present invention relates to a farnesyltransferase inhibitor and an antitumor agent containing, as an active ingredient, a piperazinedione derivative represented by formula (I):

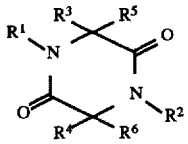
(I)

wherein $R^1$ and $R^2$ independently represent lower alkyl, lower alkoxyalkyl, substituted or unsubstituted aryl, or aralkyl; $R^3$ and $R^4$ independently represent mercapto, lower alkanoylthio, aroylthio, lower alkoxycarbonylthio, or aryloxycarbonylthio, or alternatively $R^3$ and $R^4$ are combined together to form disulfide; and $R^5$ and $R^6$ independently represent hydrogen, lower alkyl, lower alkoxyalkyl, hydroxyalkyl, lower alkanoyloxyalkyl, aroyloxyalkyl, aralkyloxyalkyl, or aralkyl.

The present invention also relates to a method for the prevention or treatment of diseases caused by the action of farnesyltransferase and a method for the prevention or treatment of tumors, which comprise administering an effective amount of a piperazinedione derivative represented by formula (I).

The present invention further relates to the use of a piperazinedione derivative represented by formula (I) for the preparation of a pharmaceutical composition which is useful for the prevention or treatment of diseases caused by the action of farnesyltransferase and the prevention or treatment of tumors.

The present invention furthermore provides piperazinedione derivatives represented by formula (I-A), formula (I-B), and formula (I-C) shown below which exhibit farnesyltransferase inhibitory activity, antibacterial activity, and antitumor activity:

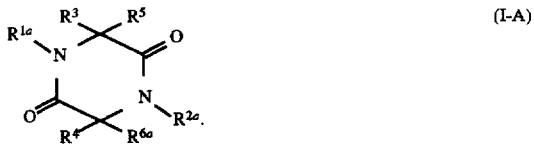

wherein $R^{1a}$ represents substituted or unsubstituted aryl; $R^{2a}$ represents lower alkyl; $R^{6a}$ represents lower alkyl, lower alkoxyalkyl, hydroxyalkyl, lower alkanoyloxyalkyl, aroyloxyalkyl, aralkyloxyalkyl, or aralkyl; and $R^3$, $R^4$, and $R^5$ have the same meanings as defined above;

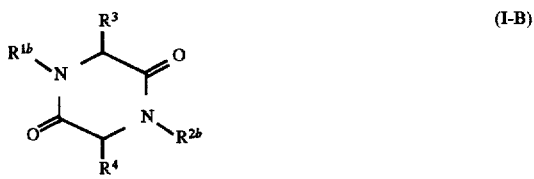

wherein $R^{1b}$ and $R^{2b}$ independently represent aralkyl; and $R^3$ and $R^4$ have the same meanings as defined above;

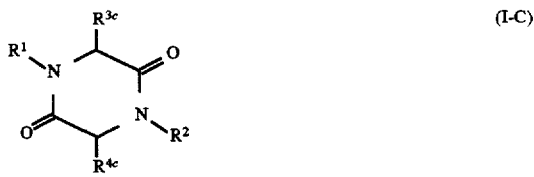

wherein $R^{3c}$ and $R^{4c}$ independently represent aroylthio, lower alkoxycarbonylthio, or aryloxycarbonylthio; and $R^1$ and $R^2$ have the same meanings as defined above.

The compounds represented by formula (I), formula (I-A), formula (I-B), and formula (I-C) are hereinafter referred to as Compounds I, Compounds I-A, Compounds I-B, and Compounds I-C, respectively. The same applies to the compounds of other formula numbers.

In the definitions of the groups in formula (I), formula (I-A), formula (I-B), and formula (I-C), the lower alkyl means a straight-chain or branched alkyl group having 1 to 6 carbon atoms, such as methyl, ethyl, propyl, isopropyl, butyl, isobutyl, sec-butyl, tert-butyl, pentyl, and hexyl. The aryl means phenyl, naphthyl, etc. The alkyl moiety of the aralkyl, lower alkanoylthio, lower alkoxycarbonylthio, hydroxyalkyl, and aroyloxyalkyl, and the two alkyl moieties of the lower alkoxyalkyl, lower alkanoyloxyalkyl, and aralkyloxyalkyl have the same meaning as the abovementioned lower alkyl. The aryl moiety of the aralkyl, aroylthio, aryloxycarbonylthio, aroyloxyalkyl, and aralkyloxyalkyl has the same meaning as the above-mentioned aryl. The substituted aryl has 1 to 3 substituents. Examples of the substituents are halogen, lower alkyl, hydroxyl, and lower alkoxy. The halogen means iodine, bromine, chlorine, or fluorine, and the alkyl moiety of the lower alkyl and lower alkoxy has the same meaning as the above-mentioned lower alkyl.

The processes for producing Compounds I are described below.

Compounds I can be synthesized according to the known method [Tetrahedron, 37, 2045 (1981)] or a method similar thereto.

1. Compound Ia, which is Compound I wherein $R^3$ and $R^4$ are both acetylthio, and $R^5$ and $R^6$ are both hydrogen; Compound Ib, which is Compound I wherein $R^3$ and $R^4$ are both mercapto, and $R^5$ and $R^6$ are both hydrogen; Compound Ic, which is Compound I wherein $R^3$ and $R^4$ are combined together to form disulfide, and $R^5$ and $R^6$ are both hydrogen; and Compound Id, which is Compound I wherein $R^3$ and $R^4$ are both lower alkanoylthio, aroylthio, lower alkoxycarbonylthio, or aryloxycarbonylthio, and $R^5$ and $R^6$ are both hydrogen, can be prepared according to the following reaction steps:

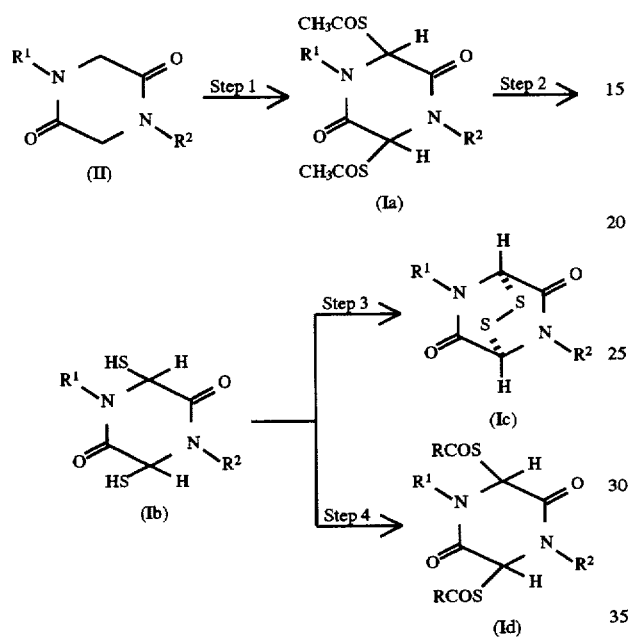

(In the formulae, R represents lower alkyl, aryl, lower alkoxy, or aryloxy; and $R^1$ and $R^2$ have the same meanings as defined above.)

The lower alkyl, aryl, lower alkoxy, and aryloxy have the same meanings as defined above, respectively.

(Step 1)

Compound Ia can be obtained by reacting Compound II with a halogenating agent, such as N-bromosuccinimide or bromine, in an inert solvent, such as carbon tetrachloride, chloroform, or dichloromethane, in the presence of a catalyst such as perbenzoic acid, and then reacting the product with a thioacetate, such as potassium thioacetate or sodium thioacetate. In the reaction of Compound II with a halogenating agent, the reaction temperature is preferably 0° to 150° C., and the reaction time is usually 30 minutes to hours. In the reaction of the product with a thioacetate, the reaction temperature is preferably 0° to 100° C., and the reaction time is usually 30 minutes to 10 hours.

(Step 2)

Compound Ib can be obtained by treating Compound Ia with an acid, such as hydrogen chloride gas, in a solvent, such as methanol or ethanol. The reaction temperature is preferably 0° to 150° C., and the reaction time is usually 10 minutes to 5 hours.

(Step 3)

Compound Ic can be obtained by oxidizing Compound Ib with 1 to 10 equivalents of an oxidizing agent, such as iodine, in an inert solvent, such as dichloromethane, chloroform, or tetrahydrofuran. The reaction temperature is preferably −30° to 100° C., and the reaction time is usually 10 minutes to 5 hours.

(Step 4)

Compound Id can be obtained by reacting Compound Ib with an acylating agent, such as an acid chloride, an acid bromide, or an acid anhydride, or a chloroformate, such as an aryl chloroformate or an alkyl chloroformate, in a solvent, such as chloroform, dichloromethane, acetonitrile, or dimethylformamide, in the presence of a base, such as pyridine, triethylamine, or diisopropylamine. The reaction temperature is preferably −30° to 100° C., and the reaction time is usually 10 minutes to 5 hours.

2. Compound Ie, which is Compound I wherein $R^3$ and $R^4$ are combined together to form disulfide, and $R^6$ is a group other than hydrogen; Compound If, which is Compound I wherein $R^3$ and $R^4$ are both mercapto, and $R^6$ is a group other than hydrogen; and Compound Ig, which is Compound I wherein $R^3$ and $R^4$ are both lower alkanoylthio, aroylthio, lower alkoxycarbonylthio, or aryloxycarbonylthio, and $R^6$ is a group other than hydrogen, can be prepared according to the following reaction steps:

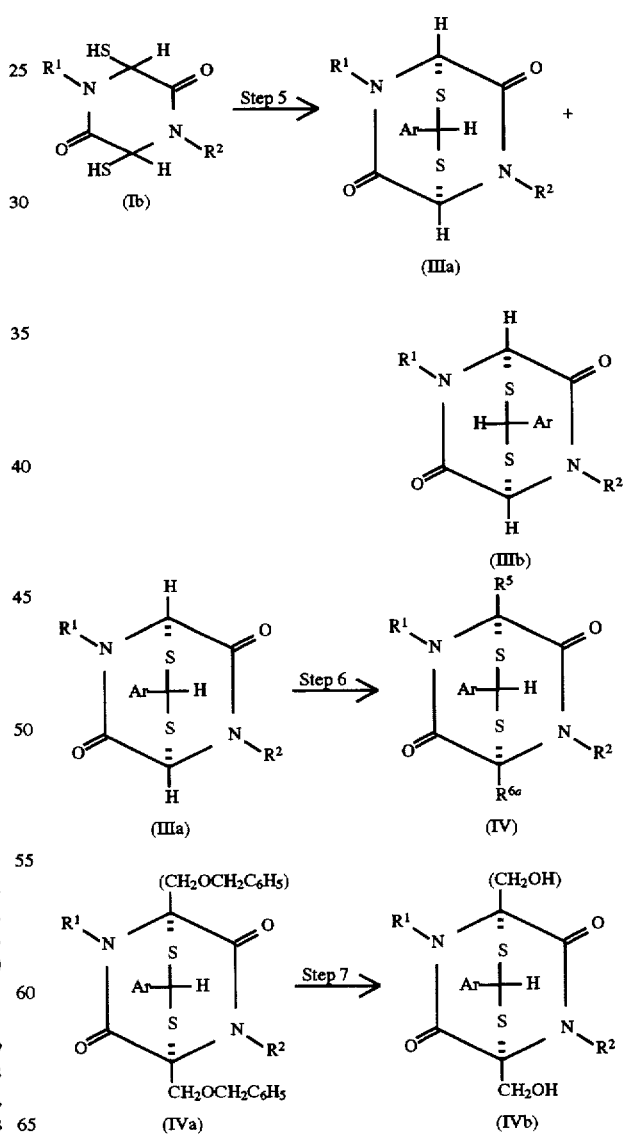

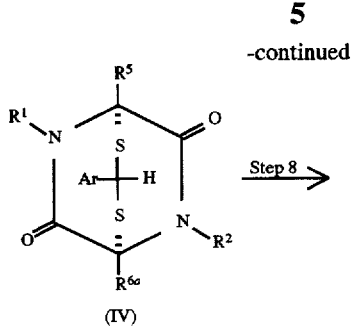

(IV)

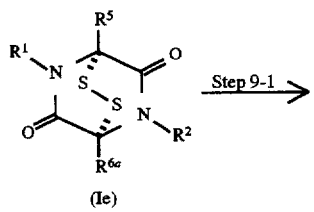

(Ie)

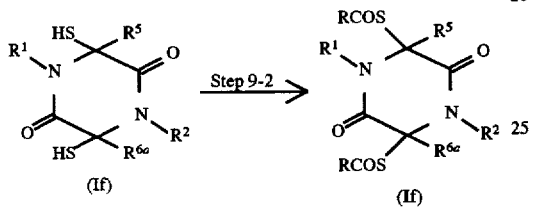

(If)            (If)

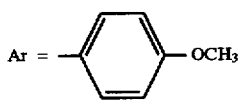

(In the formulae, $R^1$, $R^2$, $R^5$, $R^{6a}$, and R have the same meanings as defined above.)

(Step 5)

Compound IIIa and Compound IIIb can be obtained by reacting Compound Ib with p-anisaldehyde in an inert solvent, such as dichloromethane, chloroform, tetrahydrofuran, or diethyl ether, in the presence of a Lewis acid, such as boron trifluoride diethyl etherate or titanium tetrachloride. The reaction temperature is preferably –80° to 50° C., and the reaction time is usually 10 minutes to 10 hours.

Compound IIIa and Compound IIIb can be separated and purified by the methods conventionally used in organic synthesis, for example, recrystallization, and various kinds of chromatography.

(Step 6)

Compound IV can be obtained by reacting Compound IIIa and a reagent, such as chloromethyl benzyl ether, chloromethyl methyl ether, methyl iodide, or benzyl bromide, in an inert solvent, such as tetrahydrofuran, diethyl ether, or hexane, in the presence of a base, such as phenyl lithium, butyl lithium, or lithium diisopropylamide. The reaction temperature is preferably –100° to 50° C., and the reaction time is usually 10 minutes to 10 hours.

(Step 7)

Compound IVb, which is Compound IV wherein one or both of $R^5$ and $R^6$ are hydroxymethyl, can be obtained by treating Compound IVa, which is Compound IV wherein one or both of $R^5$ and $R^6$ are benzyloxymethyl, with a Lewis acid, such as boron trichloride or boron tribromide, in an inert solvent, such as dichloromethane, chloroform, tetrahydrofuran, or diethyl ether. The reaction temperature is preferably –100° to 50° C., and the reaction time is usually 10 minutes to 10 hours.

(Step 8)

Compound Ie can be obtained by oxidizing Compound IV with 1 to 2 equivalents of an oxidizing agent, such as m-chloroperbenzoic acid, peracetic acid, or hydrogen peroxide, in a solvent, such as chloroform, dichloromethane, tetrahydrofuran, or diethyl ether, to form a sulfoxide, and then treating the sulfoxide with an acid, such as perchloric acid, hydrochloric acid, or hydrobromic acid. In the oxidation, the reaction temperature is preferably –100° to 50° C., and the reaction time is usually 10 minutes to 5 hours. In the acid treatment, the reaction temperature is preferably 0 to 50° C., and the reaction time is usually 1 to 5 hours.

(Step 9)

Compound Ig can be obtained by reducing Compound Ie into a dithiol with a reducing agent, such as sodium borohydride, in a solvent, such as methanol or ethanol, to give Compound If, and then subjecting Compound If to the conditions similar to those in Step 4. In the reduction, the reaction temperature is preferably –100° to 50° C., and the reaction time is usually 10 minutes to 2 hours. Compound Ie in which one or both of $R^5$ and $R^6$ are hydroxymethyl may sometimes undergo acylation of the hydroxyl group simultaneously.

The desired compounds in the processes described above can be isolated and purified by an appropriate combination of the methods conventionally used in organic synthesis, for example, filtration, extraction, washing, drying, concentration, crystallization, and various kinds of chromatography.

Compounds I and pharmaceutically acceptable salts thereof may be in the form of adducts with water or various solvents, which can also be used as the therapeutic agents of the present invention.

The structures of typical examples of Compounds I are shown in Table 1.

TABLE 1

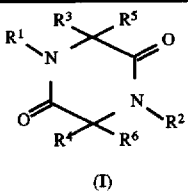

(I)

| Compd. No. | $R^1$ | $R^2$ | $R^3$ | $R^4$ | $R^5$ | $R^6$ |
|---|---|---|---|---|---|---|
| I-1 | $C_6H_5$ | $CH_3$ | $SCOCH_3$ | $SCOCH_3$ | H | H |
| I-2 | 2-$OCH_3$-$C_6H_4$ | $CH_3$ | $SCOCH_3$ | $SCOCH_3$ | H | H |
| I-3 | 3-Br-4-$OCH_3$-$C_6H_3$ | $CH_3$ | $SCOCH_3$ | $SCOCH_3$ | H | H |
| I-4 | $C_6H_5$ | $C_6H_5$ | $SCOCH_3$ | $SCOCH_3$ | H | H |
| I-5 | $CH_2OCH_3$ | $CH_2OCH_3$ | $SCOCH_3$ | $SCOCH_3$ | H | H |
| I-6 | $CH_2C_6H_5$ | $CH_2C_6H_5$ | $SCOCH_3$ | $SCOCH_3$ | H | H |
| I-7 | $C_6H_5$ | $CH_3$ | —S—S— | | H | H |
| I-8 | $C_6H_5$ | $C_6H_5$ | —S—S— | | H | H |
| I-9 | $C_6H_5$ | $C_6H_5$ | $SCOC_6H_5$ | $SCOC_6H_5$ | H | H |
| I-10 | $C_6H_5$ | $C_6H_5$ | $SCO_2C_6H_5$ | $SCO_2C_6H_5$ | H | H |
| I-11 | $C_6H_5$ | $CH_3$ | —S—S— | | H | $CH_2OCH_2C_6H_5$ |
| I-12 | $C_6H_5$ | $CH_3$ | —S—S— | | $CH_2OCH_2C_6H_5$ | $CH_2OCH_2C_6H_5$ |
| I-13 | $C_6H_5$ | $CH_3$ | —S—S— | | H | $CH_2OH$ |
| I-14 | 2-$OCH_3$-$C_6H_4$ | $CH_3$ | —S—S— | | H | $CH_2OH$ |
| I-15 | 2-$OCH_3$-$C_6H_4$ | $CH_3$ | —S—S— | | $CH_2OH$ | $CH_2OH$ |
| I-16 | $C_6H_5$ | $CH_3$ | $SCOCH_3$ | $SCOCH_3$ | H | $CH_2OCOCH_3$ |
| I-17 | $CH_2OCH_3$ | $CH_2OCH_3$ | $SCO_2C_6H_5$ | $SCO_2C_6H_5$ | H | H |
| I-18 | $CH_2C_6H_5$ | $CH_2C_6H_5$ | SH | SH | H | H |
| I-19 | $CH_2C_6H_5$ | $CH_2C_6H_5$ | —S—S— | | H | H |
| I-20 | $C_6H_5$ | $C_6H_5$ | $SCO_2C_2H_5$ | $SCO_2C_2H_5$ | H | H |
| I-21 | $C_6H_5$ | $CH_3$ | —S—S— | | $CH_2OH$ | $CH_2OH$ |

The physical properties of Compounds I are shown below. Compound I-6 and Compounds I-9 through I-21 are novel compounds and will be described in Examples.

(1) Compound I-1
   FABMS (m/z); 353 (MH⁺)
(2) Compound I-2
   FABMS (m/z); 383 (MH⁺)
(3) Compound I-3
   FABMS (m/z); 463, 461 (MH⁺)
(4) Compound I -4
   FABMS (m/z); 415 (MH⁺)
(5) Compound I-5
   FABMS (m/z); 351 (MH⁺)
(6) Compound I-7
   FABMS (m/z); 267 (MH⁺)
(7) Compound I-8
   FABMS (m/z); 329 (MH⁺)

The processes of preparation and more detailed physical data for Compound I-1, Compound I-2, and Compound I-7 are described in Japanese Published Unexamined Patent Application No. 233675/86, and those for Compound I-4 and Compound I-8 are described in German Offen. 2029306. The process for preparing Compound I-5 is described in J. Chem. Soc., Chem. Commun., 810 (1983). The process of preparation and more detailed physical data for Compound I-3 are given in Reference Example.

The structures and compound numbers of compounds shown in Reference Examples are listed in Table 2.
TABLE 2
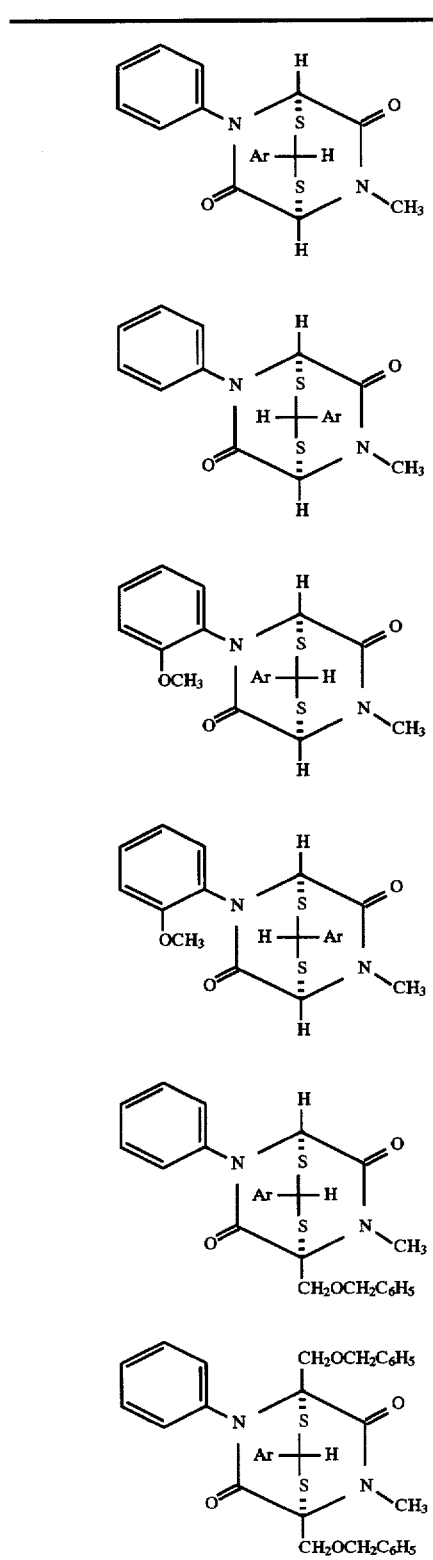
TABLE 2-continued
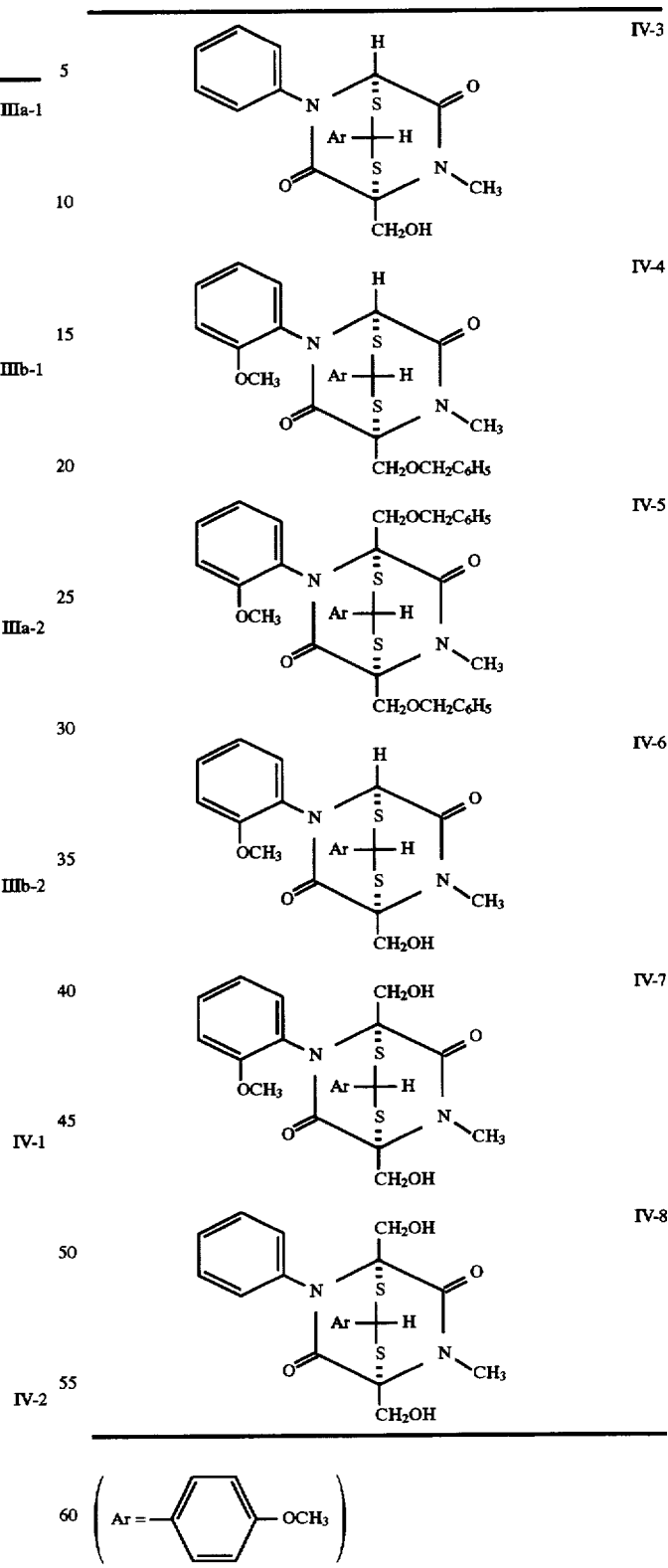
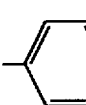
The pharmacological activities of Compounds I are shown by the following Test Examples.

TEST EXAMPLE 1

Farnesyltransferase Inhibitory Activity

An extract of minced bovine brain was subjected to column chromatography on DEAE-Sephacel (Pharmacia). The active fraction was concentrated by ultrafiltration and dialyzed against a mixture of 20 mM Tris-HCl (pH 8.0), 50 mM NaCl, 20 mM $ZnCl_2$, 1 mM dithiothreitol (DTT), and 0.2 mM phenylmethylsulfonyl fluoride (PMSF). The resulting dialysate was used as a crude enzyme liquid of farnesyltransferase (FTase). The measurement of activity was carried out by means of an FTase [$^3$H]SPA enzyme assay kit (Amersham) using the enzyme obtained by the above method. The enzyme inhibitory activity of a test sample was determined using the above-mentioned reaction system and evaluated in terms of inhibition of farnesylation of the C-terminal peptide of lamin B. The concentration of the sample inhibiting the farnesylation by 50% ($IC_{50}$) was calculated by comparing the enzyme inhibitory activity of an untreated group with those of groups treated with the sample having known concentrations.

TEST EXAMPLE 2

Anticell Activity

The anticell activity was measured using BALB 3T3 cells transformed by the oncogene H-ras (hereinafter referred to as BALB 3T3/H-ras cells).

BALB 3T3/H-ras cells were suspended in a DME medium (Nissui) containing 10% bovine fetal serum (hereinafter referred to as medium A) to a cell concentration of $3.0 \times 10^4$ cells/ml. Each well of a 96-well microtiter plate was inoculated with 0.1 ml of the cell suspension, and the system was cultured in a $CO_2$ gas incubator at 37° C. for 20 hours. To each well was added 0.1 ml of a sample (test compound) diluted appropriately with medium A, followed by culturing in the $CO_2$ gas incubator at 37° C. for 72 hours. The culture supernatant was removed, and the residue was washed once with physiological saline and treated with 0.1 ml of methanol for 10 minutes to immobilize the cells. The cells were stained with 0.1 ml of a Giemsa staining solution [Giemsa staining stock solution Merck Art9204 (Merck & Co., Inc.):physiological saline=1:10] for 5 minutes. The staining solution was removed, and the residue was washed once with 0.2 ml of water. The pigment was extracted with 0.2 ml of 0.1N hydrochloric acid, and the absorbance at 620 nm was measured with a microplate reader. The concentration of the sample inhibiting the cell growth by 50% ($IC_{50}$) was calculated by comparing the absorbance of untreated cells with those of cells treated with the sample having known concentrations.

The results of Test Example 1 and Test Example 2 are shown in Table 3.

TABLE 3

| Compound No. | $IC_{50}$ (μM) FTase Inhibitory Activity | Anti-BALB 3T3/H-ras Cell Activity |
|---|---|---|
| I-1 | 5 | 0.2 |
| I-2 | 9 | 0.5 |
| I-3 | 9 | 1.5 |
| I-4 | 12 | 0.9 |
| I-5 | 8 | 0.4 |
| I-6 | 7 | 4.0 |

TABLE 3-continued

| Compound No. | $IC_{50}$ (μM) FTase Inhibitory Activity | Anti-BALB 3T3/H-ras Cell Activity |
|---|---|---|
| I-7 | 60 | 0.2 |
| I-8 | 10 | 0.7 |
| I-9 | 9 | 3.0 |
| I-10 | 25 | 1.0 |
| I-11 | 3 | 3.0 |
| I-12 | 3 | 1.0 |
| I-13 | 5 | 0.1 |
| I-14 | 6 | 0.3 |
| I-15 | 7 | 0.3 |
| I-16 | 20 | 1.7 |
| I-17 | 5 | 0.3 |
| I-19 | 7 | — |
| I-20 | 45 | — |
| I-21 | 3 | 0.2 |

TEST EXAMPLE 3

Antibacterial Activity

The antibacterial activity was measured by the agar dilution method using a medium (pH 7) prepared by dissolving 3 g of Bacto-tryptone (Difco), 3 g of meat extract, 1 g of yeast extract, 1 g of glucose, and 16 g of agar in 1 liter of water. The antibacterial activity of Compounds I are expressed in terms of minimum growth inhibitory concentration (MIC).

The results are shown in Table 4.

TABLE 4

| Compound No. | MIC (μg/ml) CA | EF | BS |
|---|---|---|---|
| I-6 | 10 | 42 | 21 |
| I-10 | 42 | — | — |
| I-11 | 0.46 | — | 7.3 |
| I-12 | 42 | — | 42 |
| I-13 | 42 | 0.16 | 0.041 |
| I-14 | — | — | 7.3 |
| I-15 | — | 1.3 | 0.33 |
| I-16 | — | 42 | 5.2 |
| I-17 | — | — | 42 |
| I-19 | 2.6 | 83 | 83 |
| I-21 | — | 0.33 | 21 |

Note:
CA; Candida albicans ATCC 10231
EF; Enterococcus faecium ATCC 10541
BS; Bacillus subtilis No. 10707

TEST EXAMPLE 4

Antitumor Activity on Isogenic Tumor System in K-BALB Mice

The antitumor activity on an isogenic tumor system in K-BALB mice was measured according to the method described in Proc. Natl. Acad. Sci., 90, 2281 (1993). That is, an isogenic tumor in K-BALB mice was resected from a donor mouse, and a 2×2×2 (8) mm$^3$ tumor piece was transplanted to the subcutaneous site of the abdomen of a BALB/c mouse by means of a trocar. After the graft survival was confirmed on the 7th day from the transplantation, a test compound was intraperitoneally administered for 5 consecutive days from the same day. The longer diameter and shorter diameter of the tumor were measured with a sliding gauge, and the tumor volume was calculated according to the formula; (longer diameter)×(shorter diameter)$^2$/2 [Cancer Chemother. Rep., Part III, 3, 1 (1972)]. The antitumor effect was evaluated in terms of T/C, the ratio of the tumor volume of a test compound-treated group (T) to that of an untreated group (C).

The results are shown in Table 5.

TABLE 5

| Compound No. | Dose (mg/kg) | T/C |
|---|---|---|
| I-4 | 5.0 | 0.41 |
| I-13 | 0.75 | 0.44 |

When 15 mg/kg of Compound I-1 was intraperitoneally administered to a BALB/c mouse once a day for 5 consecutive days, the BALB/C mouse survived.

Compounds I and pharmaceutically acceptable salts thereof can be administered orally or parenterally either as such or in the form of various pharmaceutical compositions, such as tablets, pills, powders, granules, capsules, suppositories, injections, and infusions.

The pharmaceutical compositions having the above-mentioned dose forms are prepared in a conventional manner. For example, the compositions may contain various vehicles, lubricants, binders, disintegrators, suspending agents, isotonicity agents, emulsifiers, absorption accelerators, and the like.

Examples of the carriers which can be used in the pharmaceutical compositions are water, injectable distilled water, physiological saline, glucose, fructose, sucrose, mannitol, lactose, starch, corn starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, and glycerin fatty acid esters. These carriers are appropriately selected depending on the dose form.

The dose and the schedule of the administration vary depending on the aimed therapeutic effect, the mode of administration, the period of therapy, the age and body weight of a patient, and the like. However, the dose is usually 0.01 to 2 mg/kg per day for an adult in oral administration or parenteral administration (e.g., injection, infusion, rectal administration using suppositories, application to the skin, etc.).

Examples and Reference Examples of the present invention are shown below.

BEST MODE FOR CARRYING OUT THE INVENTION

The term "usual post-treatment" in the following Examples and Reference Examples means the following post-reaction procedure.

After the completion of reaction in each step, the reaction mixture, to which water, an acid, a buffer solution, etc. may be added if desired, is extracted with a non-aqueous solvent, such as ethyl acetate, chloroform, or diethyl ether. The extract is washed with water, an aqueous solution of sodium chloride, etc. and dried over anhydrous sodium sulfate, etc., and the solvent is removed by distillation.

EXAMPLE 1

Synthesis of Compound I-6

To 10 ml of carbon tetrachloride were added 50 mg (0.17 mmol) of 1,4-dibenzylpiperazine-2,5-dione,
N-bromosuccinimide, and 4 mg (0.017 mmol) of benzoyl peroxide, and the mixture was stirred at 70° C. for 90 minutes. The reaction mixture was cooled to room temperature, and 100 mg (0.88 mmol) of potassium thioacetate was added thereto, followed by stirring at room temperature for 2 hours. The reaction mixture was subjected to the usual post-treatment and the product was purified by thin layer chromatography (eluent; ethyl acetate/hexane=1/1) to give 23 mg (yield; 31%) of Compound I-6.

FABMS m/z; 443 (MH$^+$)

$^1$HNMR (CDCl$_3$, 100 MHz); 7.40-7.15 (m, 10H), 5.86 (s, 2H), 4.98 (d, J=15 Hz, 2H), 4.02 (d, J=15 Hz, 2H), 2.43 (s, 6H)

EXAMPLE 2

Synthesis of Compound I-9

In 2 ml of dichloromethane was dissolved 31 mg (0.095 mmol) of 3,6-dimercapto-1,4-diphenylpiperazine-2,5-dione, and 23 µl (0.2 mmol) of benzoyl chloride and 0.1 ml of pyridine were added thereto, followed by stirring at room temperature for 20 minutes. The reaction mixture was subjected to the usual post-treatment and the product was purified by thin layer chromatography (eluent; ethyl acetate/hexane=1/1) to give 48 mg (yield; 94%) of Compound I-9.

FABMS m/z; 539 (MH$^+$)

$^1$HNMR (CDCl$_3$, 100 MHz); 7.96-7.23 (m, 20H), 6.62 (s, 2H)

EXAMPLE 3

Synthesis of Compound I-10

The same procedure as in Example 2 was repeated using 40 mg (0.12 mmol) of 3,6-dimercapto-1,4-diphenylpiperazine-2,5-dione, 30 µl (0.24 mmol) of phenyl chloroformate, and 0.1 ml (1.24 mmol) of pyridine to give 27 mg (yield; 39%) of Compound I-10.

FABMS m/z; 571 (MH$^+$)

$^1$HNMR (CDCl$_3$, 100 MHz); 7.60-6.88 (m, 20H), 6.23 (s, 2H)

EXAMPLE 4

Synthesis of Compound I-11

In 2 ml of dichloromethane was dissolved 20 mg (0.04 mmol) of Compound IV-1 obtained in Reference Example 2, and 9.8 mg (70%) of m-chloroperbenzoic acid was added thereto under ice-cooling, followed by stirring at the same temperature for 15 minutes. After addition of 0.1 ml of dimethyl sulfide to the reaction mixture, 0.2 ml of a 10% methanolic solution of perchloric acid was added thereto, followed by stirring at room temperature for 18 hours. The reaction mixture was subjected to the usual post-treatment and the product was purified by thin layer chromatography (eluent; diethyl ether/hexane=4/3) to give 12 mg (yield; 77%) of Compound I-11.

FABMS m/z; 387 (MH$^+$)

$^1$HNMR (CDCl$_3$, 100 MHz); 7.54-7.20 (m, 10H), 5.65 (s, 1H), 4.75 (s, 2H), 4.29 (s, 2H), 3.22 (s, 3H)

EXAMPLE 5

Synthesis of Compound I-12

In 4 ml of dichloromethane was dissolved 105 mg (0.17 mmol) of Compound IV-2 obtained in Reference Example 3, and 41 mg (70%) of m-chloroperbenzoic acid was added thereto under ice-cooling, followed by stirring at the same temperature for 20 minutes. After addition of 0.1 ml of dimethyl sulfide to the reaction mixture, 0.3 ml of a 10% methanolic solution of perchloric acid was added thereto, followed by stirring at room temperature for 18 hours. The reaction mixture was subjected to the usual post-treatment and the product was purified by thin layer chromatography (eluent; diethyl ether) to give 46 mg (yield; 53%) of Compound I-12.

FABMS m/z; 507 (MH$^+$)

$^1$HNMR (CDCl$_3$, 100 MHz); 7.50-6.92 (m, 15H), 4.73 (bs, 2H), 4.28 (bs, 4H), 3.95 (d, J=10 Hz, 1H), 3.86 (d, J=10 Hz, 1H), 3.25 (s, 3H)

EXAMPLE 6

Synthesis of Compound I-13

In 2 ml of dichloromethane was dissolved 8 mg (0.019 mmol) of Compound IV-3 obtained in Reference Example 4, and 5.6 mg (70%) of m-chloroperbenzoic acid was added thereto under ice-cooling, followed by stirring at the same temperature for 20 minutes. After addition of 10 μl of dimethyl sulfide to the reaction mixture, 30 μl of a 10% methanolic solution of perchloric acid was added thereto, followed by stirring at room temperature for 9 hours. The reaction mixture was subjected to the usual post-treatment and the product was purified by thin layer chromatography (eluent; diethyl ether) to give 5.0 mg (yield; 88%) of Compound I-13.

FABMS m/z; 297 (MH$^+$)

$^1$HNMR (CDCl$_3$, 100 MHz); 7.55-7.25 (m, 5H), 5.66 (s, 1H), 4.36 (brs, 2H), 3.50 (br, 1H), 3.22 (s, 3H)

EXAMPLE 7

Synthesis of Compound I-14

The same procedure as in Example 6 was repeated using 20 mg (0.045 mmol) of Compound IV-6 obtained in Reference Example 7, 11 mg (70%) of m-chloroperbenzoic acid, 0.1 ml of dimethyl sulfide, and 0.1 ml of a 10% tetrahydrofuran solution of perchloric acid to give 9 mg (yield; 61%) of Compound I-14.

FABMS m/z; 327 (MH$^+$)

$^1$HNMR (CDCl$_3$, 100 MHz); 7.58-6.88 (m, 4H), 5.55 (s, 1H), 4.37 (bs, 2H), 3.88 (s, 3H), 3.22 (s, 3H)

EXAMPLE 8

Synthesis of Compound I-15

The same procedure as in Example 6 was repeated using 38 mg (0.080 mmol) of Compound IV-7 obtained in Reference Example 8, 20 mg (70%) of m-chloroperbenzoic acid, 0.1 ml of dimethyl sulfide, and 0.1 ml of a 10% tetrahydrofuran solution of perchloric acid to give 8 mg (yield; 28%) of Compound I-15.

FABMS m/z; 357 (MH$^+$)

$^1$HNMR (CDCl$_3$, 100 MHz); 7.60-6.95 (m, 4H), 4.37 (bs, 2H), 4.32 (d, J=11 Hz, 1H), 3.82 (s, 3H), 3.65 (bd, J=11 Hz, 1H), 3.24 (s, 3H)

EXAMPLE 9

Synthesis of Compound I-16

In a solvent mixture of 0.5 ml of dichloromethane and 0.3 ml of methanol was dissolved 9 mg (0.03 mmol) of Compound I-13 obtained in Example 6, and 5 mg (0.13 mmol) of sodium borohydride was added thereto, followed by stirring at room temperature for 15 minutes. The reaction mixture was subjected to the usual post-treatment, and the residue was dissolved in 1 ml of dichloromethane. To the solution were added 0.05 ml of acetic anhydride and 0.1 ml of pyridine, followed by stirring at room temperature for 2.5 hours. The reaction mixture was subjected to the usual post-treatment and the product was purified by thin layer chromatography (eluent; diethyl ether) to give 11 mg (yield; 85%) of Compound I-16.

FABMS m/z; 425 (MH$^+$)

$^1$HNMR (CDCl$_3$, 100 MHz); 7.47-7.15 (m, 5H), 6.52 (s, 1H), 4.65 (d, J=10.5 Hz, 1H), 4.41 (d, J=10.5 Hz, 1H), 3.11 (s, 3H), 2.43 (s, 3H), 2.19 (s, 3H), 2.13 (s, 3H)

EXAMPLE 10

Synthesis of Compound I-17

In 10 ml of methanol was dissolved 100 mg (0.29 mmol) of Compound I-5, and 3 ml of a 10% methanolic solution of hydrogen chloride was added thereto, followed by stirring at 50° C. for 3 hours. The solvent was removed by distillation under reduced pressure, and the resulting crude 3,6-dimercapto-1,4-dimethoxymethylpiperazine-2,5-dione was dissolved in 3 ml of dichloromethane. To the solution were added 73 μl (0.58 mmol) of phenyl chloroformate and 0.1 ml of pyridine, followed by stirring at room temperature for 4 hours. The reaction mixture was subjected to the usual post-treatment and the product was purified by thin layer chromatography (eluent; diethyl ether) to give 96 mg (yield; 65%) of Compound I-17.

FABMS m/z; 507 (MH$^+$)

$^1$HNMR (CDCl$_3$, 100 MHz); 7.50-7.10 (m, 10H), 6.04 (s, 2H), 5.17 (d, J=10.2 Hz, 2H), 4.80 (d, J=10.2 Hz, 2H), 3.38 (s, 6H)

EXAMPLE 11

Synthesis of Compound I-18

In 1.5 ml of methanol was dissolved 8 mg (0.018 mmol) of Compound I-6 obtained in Example 1, and 0.5 ml of a 10% methanolic solution of hydrogen chloride was added thereto, followed by stirring at 50° C. for 2 hours. The solvent was removed by distillation under reduced pressure, and the residue was crystallized from diethyl ether/methanol to give 5 mg (yield; 78%) of Compound I-18.

FABMS m/z; 359 (MH$^+$)

$^1$HNMR (CDCl$_3$, 100 MHz); 7.46-7.12 (m, 10H), 5.29 (d, J=14.6 Hz, 2H), 4.97 (d, J=7.0 Hz, 2H), 4.17 (d, J=14.6 Hz, 2H), 3.09 (d, J=7.0 Hz, 2H)

EXAMPLE 12

Synthesis of Compound I-19

In 1 ml of dichloromethane was dissolved 4 mg (0.011 mmol) of Compound. I-18 obtained in Example 11, and 10 mg (0.039 mmol) of iodine was added thereto, followed by stirring at room temperature for 4 hours. The reaction mixture was subjected to the usual post-treatment and the product was purified by thin layer chromatography (eluent; diethyl ether) to give 2 mg (yield; 51%) of Compound I-19.

FABMS m/z; 357 (MH$^+$)

$^1$HNMR (CDCl$_3$, 100 MHz); 7.48-7.12 (m, 10H), 5.24 (s, 2H), 4.85 (d, J=15.1 Hz, 2H), 4.49 (d, J=15.1 Hz, 2H)

EXAMPLE 13

Synthesis of Compound I-20

The same procedure as in Example 2 was repeated using 16 mg (0.048 mmol) of 3,6-dimercapto-1,4-diphenylpiperazine-2,5-dione, 20 µl (0.21 mmol) of ethyl chloroformate, and 0.1 ml (1.24 mmol) of pyridine to give 16 mg (yield; 70%) of Compound I-20.

FABMS m/z; 475 (MH$^+$)

HNMR (CDCl$_3$, 100 MHz); 7.60-7.20 (m, 10H), 6.16 (s, 2H), 4.20 (d, J=7.3 Hz, 4H), 1.22 (t, J=7.3 Hz, 6H)

EXAMPLE 14

Synthesis of Compound I-21

The same procedure as in Example 6 was repeated using 45 mg (0.10 mmol) of Compound I-8 obtained in Reference Example 10, 25 mg (70%) of m-chloroperbenzoic acid, 0.1 ml of ethylmethyl sulfide, and 0.3 ml of a 10% methanolic solution of perchloric acid to give 19 mg (yield; 58%) of Compound I-21.

FABMS m/z; 327 (MH$^+$)

$^1$HNMR (CDCl$_3$, 500 MHz); 7.53-7.24 (m, 5H), 4.41 (dd, J=12.5, 6.1 Hz, 1H), 4.33 (dd, J=12.5, 9.5 Hz, 1H), 4.03 (dd, J=12.5, 9.5 Hz, 1H), 3.84 (dd, J=12.5, 7.9 Hz, 1H), 3.60 (dd, J=7.9, 7.6 Hz, 1H), 3.44 (dd, J=9.5, 6.1 Hz, 1H), 3.26 (s, 3H)

EXAMPLE 15

Tablets

| | |
|---|---|
| Compound I-1 | 100 g |
| Lactose | 40 g |
| Corn starch | 18 g |
| Calcium carboxymethyl cellulose | 10 g |

A mixture of the above components was kneaded with a 10% solution of hydroxypropyl cellulose. The mixture was granulated by means of an extrusion granulator equipped with a basket of 1.0 mm, and magnesium stearate was added thereto to give granules for tableting. The granules were tableted in a conventional manner to prepare tablets of 8 mm in diameter each weighing 170 mg and containing 100 mg of Compound I-1.

EXAMPLE 16

Capsules

| | |
|---|---|
| Compound I-1 | 50 g |
| Lactose | 80 g |
| Potato starch | 38 g |

A mixture of the above components was kneaded with a 10% solution of hydroxypropyl cellulose and granulated in the same manner as in Example 15. Magnesium stearate was added to the granules, and the capsules each weighing 170 mg and containing 50 mg of Compound I-1 were prepared in a conventional manner.

EXAMPLE 17

Soft Capsules

Ten grams of Compound I-1 was dissolved in 100 g of soybean oil, and the solution was put into capsules in a conventional manner to give soft capsules each containing mg of Compound I-1.

EXAMPLE 18

Tablets

| | |
|---|---|
| Compound I-4 | 100 g |
| Lactose | 40 g |
| Corn starch | 18 g |
| Calcium carboxymethyl cellulose | 10 g |

Tablets of 8 mm in diameter each weighing 170 mg and containing 100 mg of Compound I-4 were prepared in the same manner as in Example 15.

EXAMPLE 19

Tablets

| | |
|---|---|
| Compound I-12 | 100 g |
| Lactose | 40 g |
| Corn starch | 18 g |
| Calcium carboxymethyl cellulose | 10 g |

Tablets of 8 mm in diameter each weighing 170 mg and containing 100 mg of Compound I-12 were prepared in the same manner as in Example 15.

EXAMPLE 20

Tablets

| | |
|---|---|
| Compound I-13 | 100 g |
| Lactose | 40 g |
| Corn starch | 18 g |
| Calcium carboxymethyl cellulose | 10 g |

Tablets of 8 mm in diameter each weighing 170 mg and containing 100 mg of Compound I-13 were prepared in the same manner as in Example 15.

EXAMPLE 21

Tablets

| | |
|---|---|
| Compound I-15 | 100 g |
| Lactose | 40 g |
| Corn starch | 18 g |
| Calcium carboxymethyl cellulose | 10 g |

Tablets of 8 mm in diameter each weighing 170 mg and containing 100 mg of Compound I-15 were prepared in the same manner as in Example 15.

EXAMPLE 22

Capsules

| | |
|---|---|
| Compound I-15 | 50 g |
| Lactose | 80 g |
| Potato starch | 38 g |

Capsules each weighing 170 mg and containing 50 mg of Compound I-15 were prepared in the same manner as in Example 16.

EXAMPLE 23

Soft Capsules

Soft capsules each containing 10 mg of Compound I-15 were prepared in the same manner as in Example 17.

EXAMPLE 24

Tablets

| | |
|---|---|
| Compound I-17 | 100 g |
| Lactose | 40 g |
| Corn starch | 18 g |
| Calcium carboxymethyl cellulose | 10 g |

Tablets of 8 mm in diameter each weighing 170 mg and containing 100 mg of Compound I-17 were prepared in the same manner as in Example 15.

REFERENCE EXAMPLE 1

Synthesis of Compound IIIa-1 and Compound IIIb-1

In 10 ml of methanol was dissolved 130 mg of Compound I-1, and 3 ml of a 10% methanolic solution of hydrogen chloride was added thereto, followed by stirring at 50° C. for 2 hours. The solvent was removed by distillation under reduced pressure, and the residue was dissolved in 12 ml of methylene chloride. To the solution were added 1 ml of p-anisaldehyde and 0.1 ml of boron trifluoride diethyl etherate, followed by stirring at room temperature for 1.5 hours. The reaction mixture was subjected to the usual post-treatment, and the p-anisaldehyde was removed by distillation under reduced pressure. The residue was purified by thin layer chromatography (eluent; chloroform) to give 59 mg (yield; 41%) of Compound IIIa-1 and 32 mg (yield; 22%) of Compound IIIa-2.

IIIa-1

FABMS m/z; 387 (MH$^+$)

$^1$HNMR (CDCl$_3$, 100 MHz); 7.6-6.8 (m, 9H), 5.45 (s, 1H), 5.22 (s, 1H), 5.04 (s, 1H), 3.81 (s, 3H), 3.28 (s, 3H)

IIIb-1

FABMS m/z; 387 (MH$^+$)

$^1$HNMR (CDCl$_3$, 100 MHz); 7.6-6.8 (m, 9H), 5.55 (s, 1H), 5.30 (s, 1H), 5.17 (s, 1H), 3.81 (s, 3H), 3.14 (s, 3H)

REFERENCE EXAMPLE 2

Synthesis of Compound IV-1

In 3 ml of anhydrous tetrahydrofuran were dissolved 35 mg (0.091 mmol) of Compound IIIa-1 obtained in Reference Example 1 and 43 mg (0.27 mmol) of benzyl chloromethyl ether, and 0.061 ml (0.11 mmol) of a 1.8M solution of phenyl lithium in cyclohexane/diethyl ether was added thereto at −78° C. The reaction mixture was subjected to the usual post-treatment and the product was purified by thin layer chromatography (eluent; diethyl ether) to give 22 mg (yield; 48%) of Compound IV-1.

$^1$HNMR (CDCl$_3$, 100 MHz); 7.6-6.8 (m, 14H), 5.52 (s, 1H), 5.08 (s, 1H), 4.73 (d, J=12 Hz, 1H), 4.55 (d, J=12 Hz, 1H), 4.24 (d, J=9.7 Hz, 1H), 3.88 (d, J=9.7 Hz, 1H), 3.80 (s, 3H), 3.33 (s, 3H)

REFERENCE EXAMPLE 3

Synthesis of Compound IV-2

In 15 ml of anhydrous tetrahydrofuran were dissolved 240 mg (0.62 mmol) of Compound IIIa-1 obtained in Reference Example 1 and 0.26 ml (1.87 mmol) of benzyl chloromethyl ether, and 0.7 ml (1.24 mmol) of a 1.8M solution of phenyl lithium in cyclohexane/diethyl ether was added thereto at −78° C. The reaction mixture was subjected to the usual post-treatment and the product was purified by silica gel column chromatography (eluent; ethyl acetate/hexane=15/85) to give 198 mg (yield; 49%) of Compound IV-2.

FABMS m/z; 627 (MH$^+$)

$^1$HNMR (CDCl$_3$, 100 MHz); 7.90-6.85 (m, 19H), 5.05 (s, 1H), 4.72 (d, J=12 Hz, 1H), 4.51 (d, J=12 Hz, 1H), 4.22 (d, J=9.7 Hz, 1H), 4.21 (d, J=11 Hz, 1H), 4.20 (bs, 2H), 3.86 (d, J=11 Hz, 1H), 3.79 (s, 3H), 3.35 (s, 3H), 3.25 (d, J=9.7 Hz, 1H)

REFERENCE EXAMPLE 4

Synthesis of Compound IV-3

In 4 ml of methylene chloride was dissolved 20 mg of Compound IV-1 obtained in Reference Example 2, and 0.5 ml of a 1M methylene chloride solution of boron trichloride was added thereto, followed by stirring at 0° C. for 1 hour. The reaction mixture was subjected to the usual post-treatment and the product was purified by thin layer chromatography (eluent; methanol/diethyl ether=1/99) to give 8.2 mg (yield; 50%) of Compound IV-3.

$^1$HNMR (CDCl$_3$, 100 MHz); 7.6-6.8 (m, 9H), 5.52 (s, 1H), 5.15 (s, 1H), 4.32 (d, J=13 Hz, 1H), 4.06 (d, J=13 Hz, 1H), 3.81 (s, 3H), 3.38 (s, 3H)

REFERENCE EXAMPLE 5

Synthesis of Compound IIIa-2 and Compound IIIb-2

The same procedure as in Reference Example 1 was repeated using 290 mg (0.76 mmol) of Compound I-2, 5 ml of a 10% methanolic solution of hydrogen chloride, 0.6 ml (4.9 mmol) of p-anisaldehyde, and 0.1 ml (0.81 mmol) of boron trifluoride diethyl etherate to give 160 mg (yield; 51%) of Compound IIIa-2 and 76 mg (yield; 24%) of Compound IIIb-2.

Compound IIIa-2

FABMS m/z; 417 (MH$^+$)

$^1$HNMR (CDCl$_3$, 100 MHz); 7.64-6.75 (m, 8H), 5.37 (s, 1H), 5.22 (s, 1H), 5.01 (s, 1H), 3.86 (s, 3H), 3.81 (s, 3H), 3.28 (s, 3H)

Compound IIIb-2

FABMS m/z; 417 (MH$^+$)

$^1$HNMR (CDCl$_3$, 100 MHz); 7.60-6.78 (m, 8H), 5.93 (s, 1H), 5.17 (s, 1H), 5.12 (s, 1H), 3.91 (s, 3H), 3.82 (s, 3H), 3.14 (s, 3H)

REFERENCE EXAMPLE 6

Synthesis of Compound IV-4 and Compound IV-5

In 3 ml of anhydrous tetrahydrofuran were dissolved 80 mg (0.19 mmol) of Compound IIIa-2 obtained in Reference Example 5 and 60 mg (0.38 mmol) of benzyl chloromethyl ether, and 0.2 ml (0.38 mmol) of a 1.8M solution of phenyl lithium in cyclohexane/diethyl ether was added thereto at −78° C. The reaction mixture was subjected to the usual post-treatment and the product was purified by silica gel column chromatography (eluent; ethyl acetate/hexane=15/85) to give 34 mg (yield; 33%) of Compound IV-4 and 43 mg (yield; 34%) of Compound IV-5.

Compound IV-4

FABMS m/z; 537 (MH$^+$)

$^1$HNMR (CDCl$_3$, 100 MHz); 7.60-6.65 (m, 13H), 5.48 (s, 1H), 5.11 (s, 1H), 4.70 (d, J=11 Hz, 1H), 4.50 (d, J=11 Hz, 1H), 4.22 (d, J=10 Hz, 1H), 3.88 (d, J=10 Hz, 1H), 3.85 (s, 3H), 3.79 (s, 3H), 3.34 (s, 3H)

Compound IV-5

$^1$HNMR (CDCl$_3$, 100 MHz); 7.85-6.70 (m, 18H), 5.02 (s, 1H), 4.80-3.22 (m, 8H), 3.78 (s, 3H), 3.52 (s, 3H), 3.35 (s, 3H)

REFERENCE EXAMPLE 7

Synthesis of Compound IV-6

The same procedure as in Reference Example 4 was repeated using 30 mg (0.056 mmol) of Compound IV-4 obtained in Reference Example 6 and 0.1 ml of a 1M dichloromethane solution of boron trichloride to give 21 mg (yield; 84%) of Compound IV-6.

FABMS m/z; 447 (MH$^+$)

$^1$HNMR (CDCl$_3$, 100 MHz); 7.60-6.75 (m, 8H), 5.45 (s, 1H), 5.15 (s, 1H), 4.27 (d, J=13 Hz, 1H), 4.03 (d, J=13 Hz, 1H), 3.86 (s, 3H), 3.80 (s, 3H), 3.37 (s, 3H)

REFERENCE EXAMPLE 8

Synthesis of Compound IV-7

The same procedure as in Reference Example 4 was repeated using 70 mg (0.11 mmol) of Compound IV-5 obtained in Reference Example 6 and 0.5 ml of a 1M dichloromethane solution of boron trichloride to give 39 mg (yield; 74%) of Compound IV-7.

FABMS m/z; 477 (MH$^+$)

$^1$HNMR (CDCl$_3$, 100 MHz); 7.90-6.75 (m, 8H), 5.13 (s, 1H), 4.20-3.60 (m, 4H), 3.82 (s, 3H), 3.81 (s, 3H), 3.40 (s, 3H), 2.49 (br, 2H)

REFERENCE EXAMPLE 9

Synthesis of Compound I-3

To 50 ml of carbon tetrachloride were added 1.3 g (5.56 mmol) of 1-(2-methoxyphenyl)-4-methylpiperazine-2,5-dione, 2.47 g (13.9 mmol) of N-bromosuccinimide, and 67 mg (0.28 mmol) of benzoyl peroxide, followed by stirring at 70° C. for 2 hours. The reaction mixture was cooled to room temperature, and 2.0 g (17.5 mmol) of potassium thioacetate was added thereto, followed by stirring at room temperature for 3 hours. Insoluble matters were removed by filtration, and the solvent was removed by distillation under reduced pressure. The residue was purified by silica gel column chromatography (eluent; chloroform/hexane=5/1) to give 230 mg (yield; 9%) of Compound I-3. The above reaction also afforded 900 mg (yield; 42%) of Compound I-2 as the main product.

FABMS m/z; 463, 461 (MH$^+$)

$^1$NMR (CDCl3, 400 MHz); 7.44 (dd, J=8.8, 2.4 Hz, 1H), 7.28 (d, J=2.4 Hz, 1H), 6.88 (d, J=8.8 Hz, 1H), 6.13 (s, 1H), 5.88 (s, 1H), 3.89 (s, 3H), 3.02 (s, 3H), 2.52 (s, 3H), 2.31 (s, 3H)

REFERENCE EXAMPLE 10

Synthesis of Compound IV-8

The same procedure as in Reference Example 4 was repeated using 100 mg (0.16 mmol) of Compound IV-2 obtained in Reference Example 3 and 0.8 ml of a 1M dichloromethane solution of boron trichloride to give 48 mg (yield; 67%) of Compound IV-8.

FABMS m/z; 447 (MH$^+$)

$^1$HNMR (CDCl$_3$, 100 MHz); 7.85-6.80 (m, 9H), 5.24 (s, 1H), 4.40-3.40 (m, 4H), 3.81 (s, 3H), 3.41 (s, 3H), 2.30 (br, 2H)

INDUSTRIAL APPLICABILITY

According to the present invention, there is provided a farnesyltransferase inhibitor having a piperazinedione skeleton which is useful as a pharmaceutical.

We claim:

1. A piperazinedione derivative represented by formula (I-A):

$$R^{1a}\text{-N}\begin{pmatrix}R^3 & R^5\\ & \\ R^4 & R^{6a}\end{pmatrix}\text{N-}R^{2a}\quad\text{(I-A)}$$

wherein $R^{1a}$ represents carbocyclic aryl of 6 to 10 carbon atoms optionally substituted with 1 to 3 substituents selected from the group consisting of halogen, lower alkyl of 1 to 6 carbon atoms, hydroxyl, and lower alkoxy of 1 to 6 carbon atoms; $R^{2a}$ represents lower alkyl of 1 to 6 carbon atoms; $R^{6a}$ represents lower alkoxyalkyl in which the two alkyl moieties are independently lower alkyl of 1 to 6 carbon atoms, hydroxyalkyl of 1 to 6 carbon atoms, lower alkanoyloxyalkyl in which the two alkyl moieties are independently lower alkyl of 1 to 6 carbon atoms, aroyloxyalkyl in which the aryl moiety is carbocyclic aryl of 6 to 10 carbon atoms and the alkyl moiety is lower alkyl of 1 to 6 carbon atoms, aralkyloxyalkyl in which the aryl moiety is carbocyclic aryl of 6 to 10 carbon atoms and the two alkyl moieties are independently lower alkyl of 1 to 6 carbon atoms, or aralkyl in which the aryl moiety is carbocyclic aryl of 6 to 10 carbon atoms and the alkyl moiety is lower alkyl of 1 to 6 carbon atoms; $R^3$ and $R^4$ independently represent mercapto, lower alkanoylthio of 2 to 7 carbon atoms, aroylthio in which the aryl moiety is carbocyclic aryl of 6 to 10 carbon atoms, lower alkoxycarbonylthio of 2 to 7 carbon atoms, or aryloxycarbonylthio in which the aryl moiety is carbocyclic aryl of 6 to 10 carbon atoms, or alternatively $R^3$ and $R^4$ are combined together to form disulfide; and $R^5$ represents hydrogen, lower alkyl of 1 to 6 carbon atoms, lower alkoxyalkyl in which the two alkyl moieties are independently lower alkyl of 1 to 6 carbon atoms, hydroxyalkyl of 1 to 6 carbon atoms, lower alkanoyloxyalkyl in which the two alkyl moieties are independently lower alkyl of 1 to 6 carbon atoms, aroyloxyalkyl in which the aryl moiety is carbocyclic aryl of 6 to 10 carbon atoms and the alkyl moiety is lower alkyl of 1 to 6 carbon atoms, aralkyloxyalkyl in which the aryl moiety is carbocyclic aryl of 6 to 10 carbon atoms and the two alkyl moieties are independently lower alkyl of 1 to 6 carbon atoms, or aralkyl in which the aryl moiety is carbocyclic aryl of 6 to 10 carbon atoms and the alkyl moiety is lower alkyl of 1 to 6 carbon atoms.

2. A piperazinedione derivative according to claim 1, wherein $R^3$ and $R^4$ are combined together to form disulfide; $R^5$ represents hydrogen, hydroxyalkyl of 1 to 6 carbon atoms or aralkyloxyalkyl in which the aryl moiety is carbocyclic aryl of 6 to 10 carbon atoms and the two alkyl moieties are independently lower alkyl of 1 to 6 carbon atoms; and $R^{6a}$ represents hydroxyalkyl of 1 to 6 carbon atoms or aralkyloxyalkyl in which the aryl moiety is carbocyclic aryl of 6 to 10 carbon atoms and the two alkyl moieties are independently lower alkyl of 1 to 6 carbon atoms.

3. A piperazinedione derivative represented by formula (I-B):

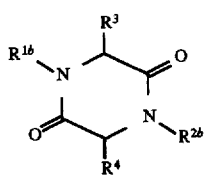

(I-B)

wherein $R^{1b}$ and $R^{2b}$ independently represent aralkyl in which the aryl moiety is carbocyclic aryl of 6 to 10 carbon atoms and the alkyl moiety is lower alkyl of 1 to 6 carbon atoms; and $R_3$ and $R_4$ independently represent mercapto, lower alkanoylthio of 2 to 7 carbon atoms, aroylthio in which the aryl moiety is carbocyclic aryl of 6 to 10 carbon atoms, lower alkoxycarbonylthio of 2 to 7 carbon atoms, or aryloxycarbonylthio in which the aryl moiety is carbocyclic aryl of 6 to 10 carbon atoms, or alternatively $R^3$ and $R^4$ are combined together to form disulfide.

4. A piperazinedione derivative represented by formula (I-C):

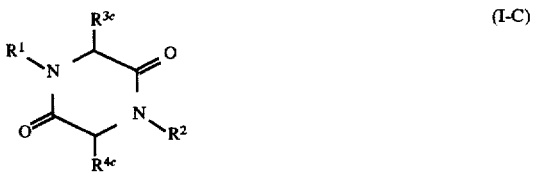

(I-C)

wherein $R^{3c}$ and $R^{4c}$ independently represent aroylthio in which the aryl moiety is carbocyclic aryl of 6 to 10 carbon atoms, lower alkoxycarbonylthio of 2 to 7 carbon atoms, or aryloxycarbonylthio in which the aryl moiety is carbocyclic aryl of 6 to 10 carbon atoms; and $R^1$ and $R^2$ independently represent lower alkyl of 1 to 6 carbon atoms, lower alkoxyalkyl in which the two alkyl moieties are independently lower alkyl of 1 to 6 carbon atoms, carbocyclic aryl of 6 to 10 carbon atoms optionally substituted with 1 to 3 substituents selected from halogen, lower alkyl of 1 to 6 carbon atoms, hydroxyl, and lower alkoxy of 1 to 6 carbon atoms, or aralkyl in which the aryl moiety is carbocyclic aryl of 6 to 10 carbon atoms and the alkyl moiety is lower alkyl of 1 to 6 carbon atoms.

5. A piperazinedione derivative according to claim 4, wherein $R^1$ and $R^2$ independently represent lower alkoxyalkyl in which the two alkyl moieties are independently lower alkyl of 1 to 6 carbon atoms; and $R^{3c}$ and $R^{4c}$ independently represent aryloxycarbonylthio in which the aryl moiety is carbocyclic aryl of 6 to 10 carbon atoms.

* * * * *